United States Patent
Herbert

(10) Patent No.: US 7,236,823 B2
(45) Date of Patent: Jun. 26, 2007

(54) PORTABLE DEFIBRILLATORS

(75) Inventor: Kevin Herbert, Gloucestershire (GB)

(73) Assignees: Desmond Bryan Mills, Gloucestershire (GB); Malcolm Bradley Mills, Gloucestershire (GB); Stephen Colin Brown, Gloucestershire (GB)

( * ) Notice: Subject to any disclaimer, the term of this patent is extended or adjusted under 35 U.S.C. 154(b) by 35 days.

(21) Appl. No.: 10/497,181

(22) PCT Filed: Nov. 28, 2002

(86) PCT No.: PCT/GB02/05361

§ 371 (c)(1),
(2), (4) Date: Dec. 28, 2004

(87) PCT Pub. No.: WO03/047692

PCT Pub. Date: Jun. 12, 2003

(65) Prior Publication Data

US 2005/0085861 A1    Apr. 21, 2005

(30) Foreign Application Priority Data

Nov. 28, 2001    (GB) .................................. 0128431.4

(51) Int. Cl.
*A61N 1/00*    (2006.01)
(52) U.S. Cl. ........................................................ 607/8
(58) Field of Classification Search ................. 607/42, 607/1, 4–8, 27–29, 50
See application file for complete search history.

(56) References Cited

U.S. PATENT DOCUMENTS

| | | | |
|---|---|---|---|
| 5,249,573 A | 10/1993 | Lopin et al. | |
| 5,800,460 A | 9/1998 | Mydynski et al. | |
| 5,879,374 A * | 3/1999 | Powers et al. | 607/5 |
| 6,073,085 A | 6/2000 | Kou et al. | |
| 6,141,584 A * | 10/2000 | Rockwell et al. | 607/5 |
| 6,169,387 B1 | 1/2001 | Kaib | |
| 6,266,562 B1 | 7/2001 | Leyde | |
| 6,501,986 B1 * | 12/2002 | Schaldach et al. | 607/5 |

* cited by examiner

*Primary Examiner*—George Manuel
(74) *Attorney, Agent, or Firm*—Young & Thompson

(57) ABSTRACT

A portable defibrillator includes a self-test circuit in which electrical energy is discharged from one or a bank of capacitors to a charge receiving circuit which recycles the energy to a rechargeable battery to prolong the original battery charge. A charge receiving circuit may contain a relatively high Ohmic value/low Wattage resistor such that the discharge occurs over a relatively long period of time, rendering a heat sink unnecessary. The resistor may be a single high value resistor or a network of plural smaller value resistors. Optional switching of the discharge electrical energy during a self-test either recycles it to the rechargeable battery or discharges it through the resistor. The self-test may be carried out on a bank of capacitors in rotation, discharging energy from one capacitor into the next such that all capacitors are charged and discharged from substantially a single power input.

9 Claims, 5 Drawing Sheets

PORTABLE DEFIBRILLATORS

As is well known, a defibrillator is a therapeutic device used to treat certain cardiac irregularities such as ventricular fibrillation and pulse-less ventricular tachycardia where one or more high energy electrical pulses from a capacitor bank are discharged into a patient via a pair of electrodes positioned on the patient's chest. Due to the complex waveform of such pulses and the need to deliver them at specific points in time following an assessment of the patient's condition, which may be done automatically by the defibrillator or manually, it is essential that the whole of the defibrillator circuitry is tested at regular intervals to guarantee that a lifesaving pulse may be given safely and effectively. This has traditionally been achieved by discharging the pulse across a load resistor of, typically, 50 ohms, in order to mimic the pulse which would otherwise be discharged into a patient.

However, because the discharge of electrical energy is very high (anywhere up to 360 Joules) and is delivered in a very short time (typically 5 to 20 milliseconds), the peak power requirement of the load resistor is quite substantial, exceeding 72 kW (360 Joules over 5 milliseconds). A consequence of this is that during a discharge there is significant resistive heating of the discharge resistor such that it is customary to provide a heat sink around it, which may take the form of an aluminum or copper sleeve incorporating heat radiating fins.

A further consequence of having such traditional self-test methods is that the physical size of the discharge resistor is relatively large and may use up a substantial portion of the circuitry housing which, along with the traditional use of a heat sink, help to make the defibrillator bulky and heavy to handle, as well as being expensive to produce and maintain. This problem is exacerbated by the fact that a full electrical discharge into the discharge resistor has a correspondingly large drain on the battery power source and up to 400 Joules per discharge are typically lost during a self-test. This results in the requirement for a relatively large battery source, which further adds to the weight and size and hence detracts from the portability of the defibrillator.

The present invention is derived in part from the realisation that with the use of a processor to calculate projected characteristics of a pulse, even if discharged over a relatively long period, it is not necessary for the pulse to be discharged over such short periods during a self-test in order for an accurate assessment of the ability of the defibrillator to deliver a lifesaving pulse when required. Also, it would be advantageous to provide a defibrillator which is relatively compact and lightweight, and may therefore be less expensive to produce and maintain.

In accordance with a first aspect of the invention there is provided a portable defibrillator which includes a processor and associated self-test circuit in which during the self-test electrical energy is discharged from one or a bank of capacitors to a charge receiving circuit which recycles the energy back to a rechargeable battery supply to thereby prolong the original charge within the battery.

According to an alternative, second, aspect of the invention there is provided a portable defibrillator which includes a processor and associated self-test circuit in which during the self-test electrical energy is discharged from one or a bank of capacitors to a charge receiving circuit containing a relatively high Ohmic value/low Wattage discharge resistor means (hereafter "high value resistor means") such that the discharge occurs over a relatively long period of time as compared to traditional methods using a low Ohmic value/ high Wattage resistor (hereafter "low value resistor") and associated heat sink. The high value resistor means may be a single high value resistor, but in a refinement to this concept a network of two or more smaller value resistors may be provided instead which collectively provide a relatively high total resistance to the electric pulse discharged by the defibrillator during a self-test.

As will be appreciated, the concepts of the first and second aspects of the invention may be incorporated into the same device with provision being made in the circuitry permitting optional switching of the capacitor discharge pulse so that it is either recycled directly back to a rechargeable battery supply, if such is present in the defibrillator, or is directed to the high value resistor means, whether or not the defibrillator is powered by rechargeable batteries. This switching may be carried out through the use of e.g. a micro-controller, but could also be by other means including a manually operated switch.

The recycling circuit option according to the first aspect of the invention is chosen where rechargeable batteries are in use and energy needs to be conserved because of self-tests occurring when the batteries are not on charge. Here, the switching circuit would direct the capacitor discharge pulse during the self-test through a DC:DC conversion circuit and back to the battery. Measurement of characteristics of the pulse during the self-test could occur either at the capacitor end of the circuit by measuring the charge or voltage drop across one or more of the capacitors, or at the recycling stage.

The option of switching the-capacitor discharge pulse to the high value resistor means can be used where battery energy need not or cannot be conserved, such as where the batteries are non-rechargeable primary batteries, or if the self-test were occurring whilst rechargeable batteries were being charged from some other source, such as a mains electricity supply. In this case, the switching circuit would direct the capacitor discharge pulse from the capacitors to the high value resistor means, whether it be a single high value resistor or a network of two or more smaller value resistors which collectively provide the desired high Ohmic value/low Wattage resistance, during which measurement of characteristics of the discharge pulse could be taken at either the capacitor end of the circuit by measuring the charge or voltage drop across one or more of the capacitors, or at the load stage i.e. across the high value resistor means.

In a third aspect of the invention the self test is carried out on a bank of capacitors in rotation such that for one self-test one capacitor is fully charged until a predetermined energy level is reached whilst the remaining capacitors in the bank are not, or may be only partially charged, and then following discharge during a self-test, the next capacitor in the bank is fully charged for discharge during the next self-test, the cycle repeating in sequence.

In a fourth aspect of the invention a single capacitor from a bank of capacitors is fully charged using the capacitor rotation described in the third aspect of the invention, but during the self-test is discharged into the next capacitor, and so on, until all of the capacitors in the capacitor bank have been charged and discharged, but only from substantially a single power input. Hence, if there are four capacitors in the capacitor bank the self-test requires only 25%, before capacitor leakage losses, of the energy that would otherwise be required for a self-test of the entire capacitor bank at the same time.

The invention will now be described, by way of example only, with reference to the accompanying drawings in which.

Figure 1:
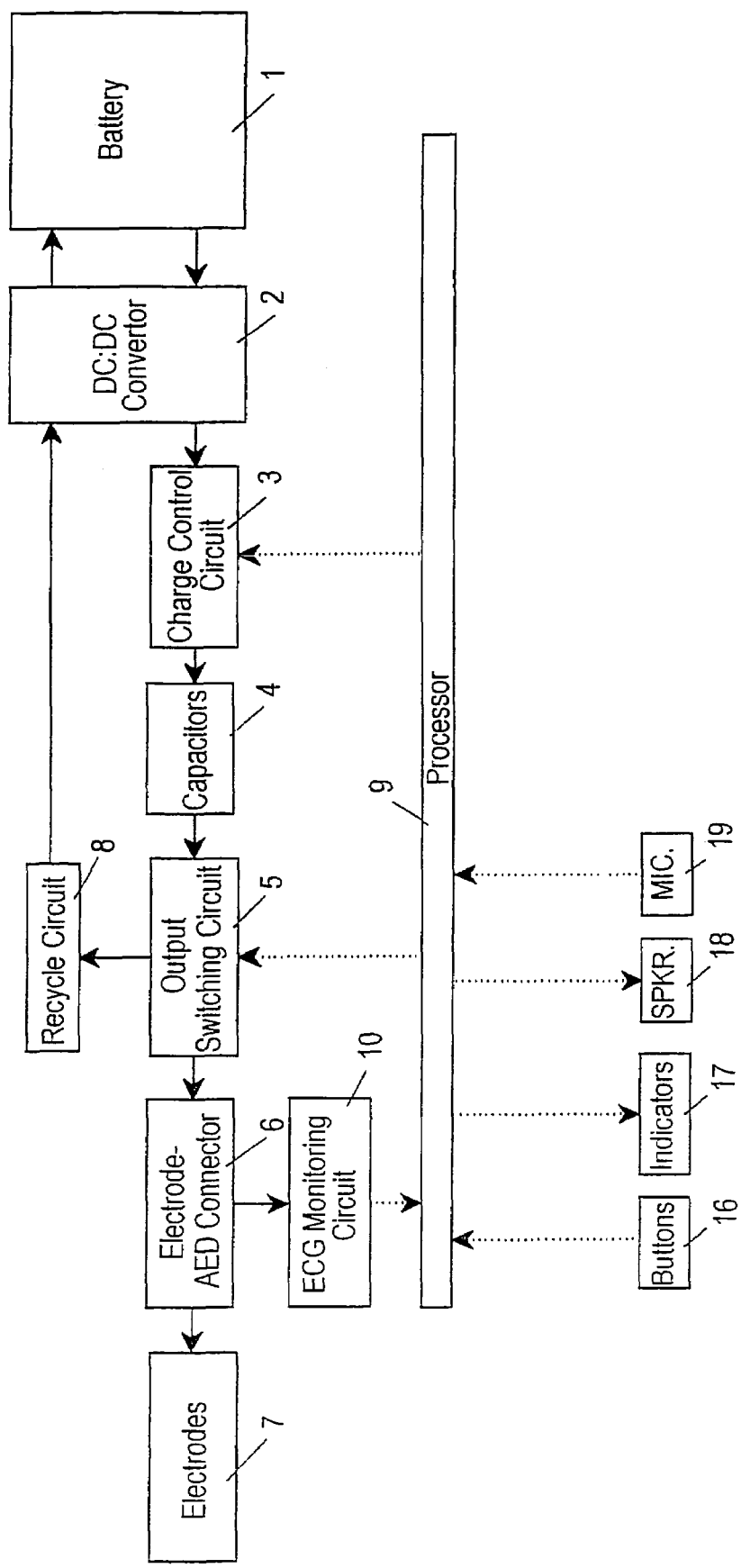
FIG. 1 is a schematic block diagram of defibrillator circuitry in accordance with a first embodiment of the invention.

Referring firstly to FIG. 1 there is shown a block diagram of a circuit for use in a portable defibrillator according to a first embodiment of the invention, which includes a rechargeable battery power source 1, a switch mode DC:DC converter 2 which in one aspect converts low voltage current from the battery 1, typically 12 volts, to high voltage current to a charge control circuit 3, typically 500 volts, which, in turn, is used to charge a capacitor bank 4 to a required energy level for delivering e.g. an 80 A pulse, in a manner to be described. The capacitor bank 4 is connected to an output switching circuit 5 which provides for a discharge from-the capacitor bank 4 to be either fed to an automated external defibrillator (AED) connector 6 for discharging an electrical pulse to a patient by means of a pair of electrodes 7 if certain predetermined parameters are met, or instead to a recycle circuit 8 for recycling the pulse back to the battery 1 via the DC:DC converter 2 in a manner to be described.

The defibrillator also includes a central processing unit 9 for receiving and processing signals from an ECG monitoring circuit 10, as well as carrying out other functions to be described. If the processor 9 recognises the ECG signal to be indicative of a shockable rhythm (such as Ventricular Fibrillation or Ventricular Tachycardia for example) it instructs the charging circuit to begin charging the capacitor bank 4 from the output of the DC:DC converter 2. When the correct charge level has been reached the processor 9 (whether automatically or semi-automatically under command from the user) instructs the output switching circuit 5 to discharge the pulse across the electrodes 7 in a manner aimed e.g. to defibrillate a patient.

The processor 9 may also communicate the status of the patient to the defibrillator user through indicators 17 or a loudspeaker 18. In response, the user can select and control the defibrillator device via the processor 9 by use of buttons 16, and a microphone 19 can be used to input an audio message to the device for subsequent replay through the loudspeaker 18. In addition, the processor 9 may also form part of a self-test circuit for measuring and monitoring electrical energy discharged from the capacitor bank 4, either within the capacitor circuit or the recycle circuit, the circuit including the battery 1, DC:DC converter 2, charge control circuit 3, capacitor bank 4, output switching circuit 5 and recycle circuit 8.

Figure 2:
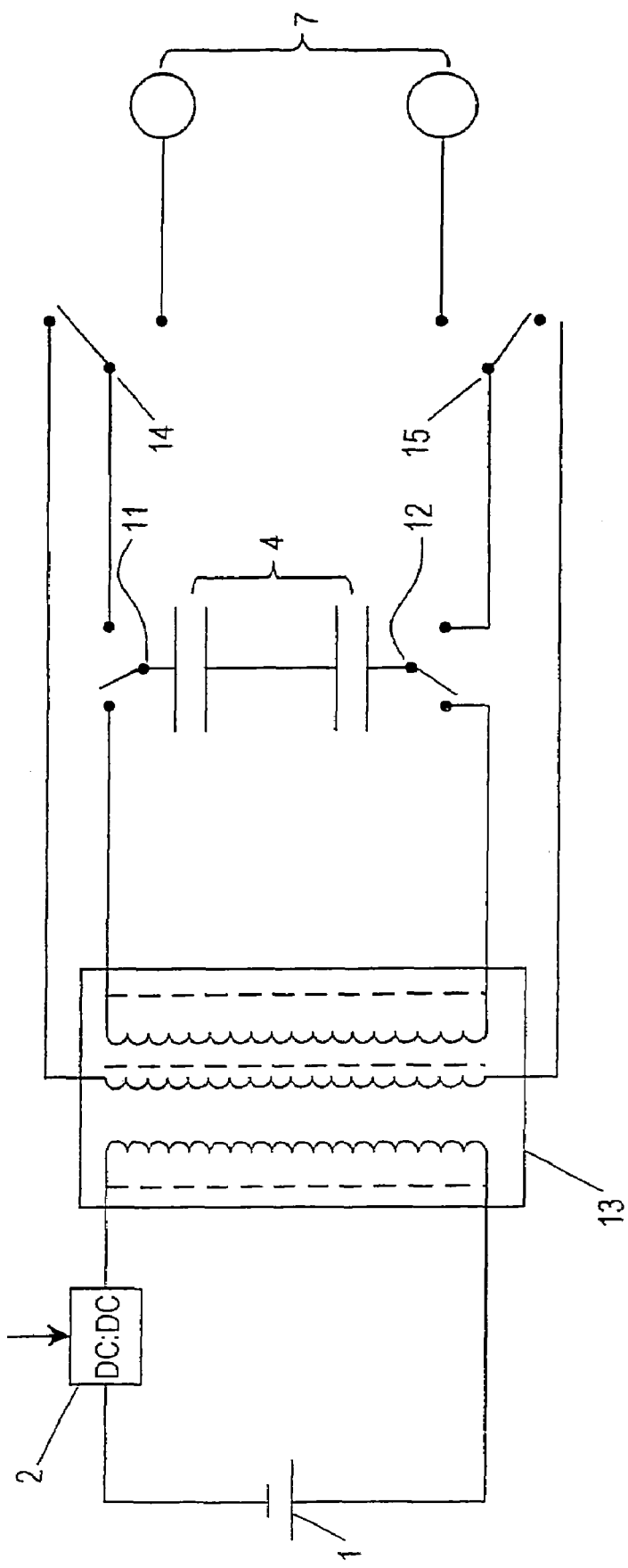
FIG. 2 is a simplified circuit diagram of part of the circuitry of FIG. 1.

Turning now to FIG. 2, there is shown a simplified circuit diagram for recharging the battery 1 following a self-test and which forms part of the recycle circuit 8 shown in FIG. 1, where like parts are numbered the same. The circuit includes, in this embodiment, a bank of two capacitors 4 and a pair of electrodes 7 for placing onto the chest of a patient prior to delivery of an electric shock. In this circuit switches 11,12 are shown closed for facilitating charging of the capacitor bank 4 via a three-coil transformer 13, and are hence open against delivering a charge from the capacitor bank 4. Switches 14, 15 are shown closed for returning a charge from the capacitor bank 4 when the switches 11, 12 are closed for delivering a charge from the capacitor bank 4. When this happens, following a self-test, the charge from the capacitor bank 4 is returned to the transformer 13 and, via the DC:DC converter 2 which reduces the charge from, typically, 2000 volts down to 12 volts, back to the battery 1.

As will be appreciated, when the switches 11, 12 are closed for delivering a pulse of electricity from the capacitor bank 4, switches 14 and 15 can also be closed for delivering that pulse to the electrodes 7 and hence to a patient onto which they have been placed.

Hence, in this first embodiment of the invention, it will be appreciated that rather than wasting the electrical discharge during a self-test and therefore incurring a drain from the battery 1, it can be fed back into the battery, so as to be more efficient, thereby permitting smaller and/or fewer batteries to be used. For a typical discharge the defibrillator discharge recycle circuit may provide up to 50% of the pulse back to the rechargeable battery pack.

Figure 3:
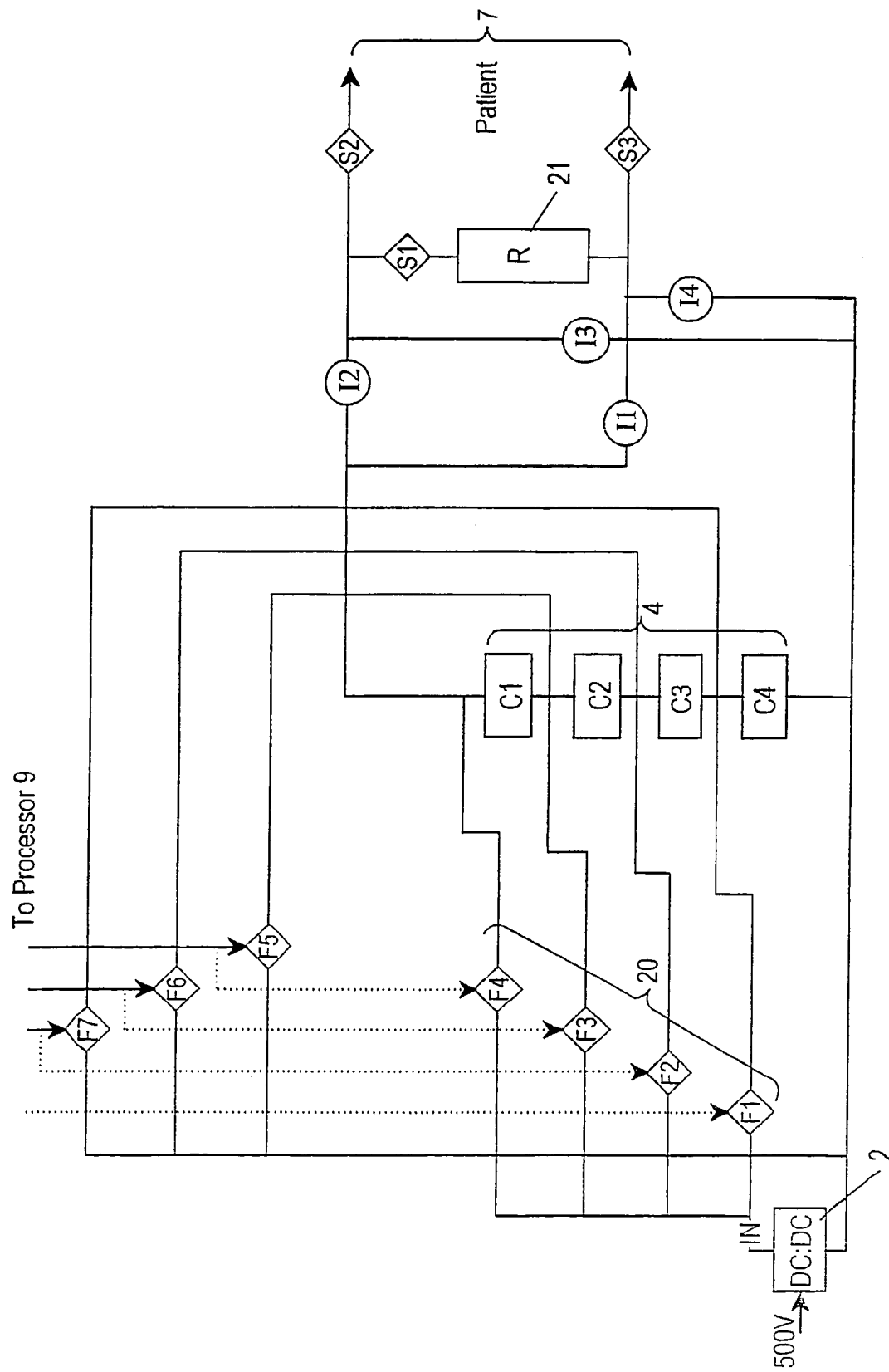
FIG. 3 is a schematic circuit diagram of second, third and fourth embodiments of the invention.

In FIG. 3 there is shown part of a circuit diagram for a defibrillator according to a second, alternative, embodiment of the invention which in this case includes a bank 4 of four capacitors (C1, C2, C3 and C4) which are each activated by controls from the processor 9 (not shown) via a bank of respective field effect transistor (FET) switches 20 (F1, F2, F3 and F4). In this case the recycle circuit 8 of FIGS. 1 and 2 has been replaced by an internal load in the form of high value resistor means, being a single high value resistor 21 typically of between 500K Ohm/10 Watts and 1M Ohm/5 Watts rather than, as is conventionally the case, the use of e.g. a 50 Ohm/72 K Watt resistor which would otherwise be required for a self-test discharge to test the integrity and viability of the defibrillator components. In this case such may also include insulated gate bipolar transistor (IGBT) switches (I1, I2, I3 and I4) and silicon controlled rectifier (SCR) switches (S1, S2 and S3).

As will be understood by those skilled in the art, by using such a high value resistor 21 the initial peak current during a self-test discharge from the capacitor bank 4 is reduced to a fraction of its initial value as compared to the use of a low value resistor and hence the overall average power loss is also dramatically decreased over time. During this period and/or afterwards, the processor 9 can be used to calculate whether measured characteristics of the discharged pulse, if given in a real-time lifesaving situation at the required power level, are satisfactory for the purposes of the self-test. A consequence of this is that the resistor 21 typically only has to handle e.g. 10 watts at 500K Ohms or 5 watts at 1M Ohm with peak current values of 4 mA and 2 mA respectively from a typical discharge pulse, such that the average discharge times across resistor 21 for these values may be 16.5 minutes and 33 minutes respectively, ignoring capacitor leakage losses.

Accordingly, by the use of a very high value resistor 21 it will be apparent that resistive heating is minimised such that the need for a heat sink, with its attendant bulk and mass, is obviated, thereby making it possible to provide a defibrillator which is relatively compact and lightweight.

Figure 4:
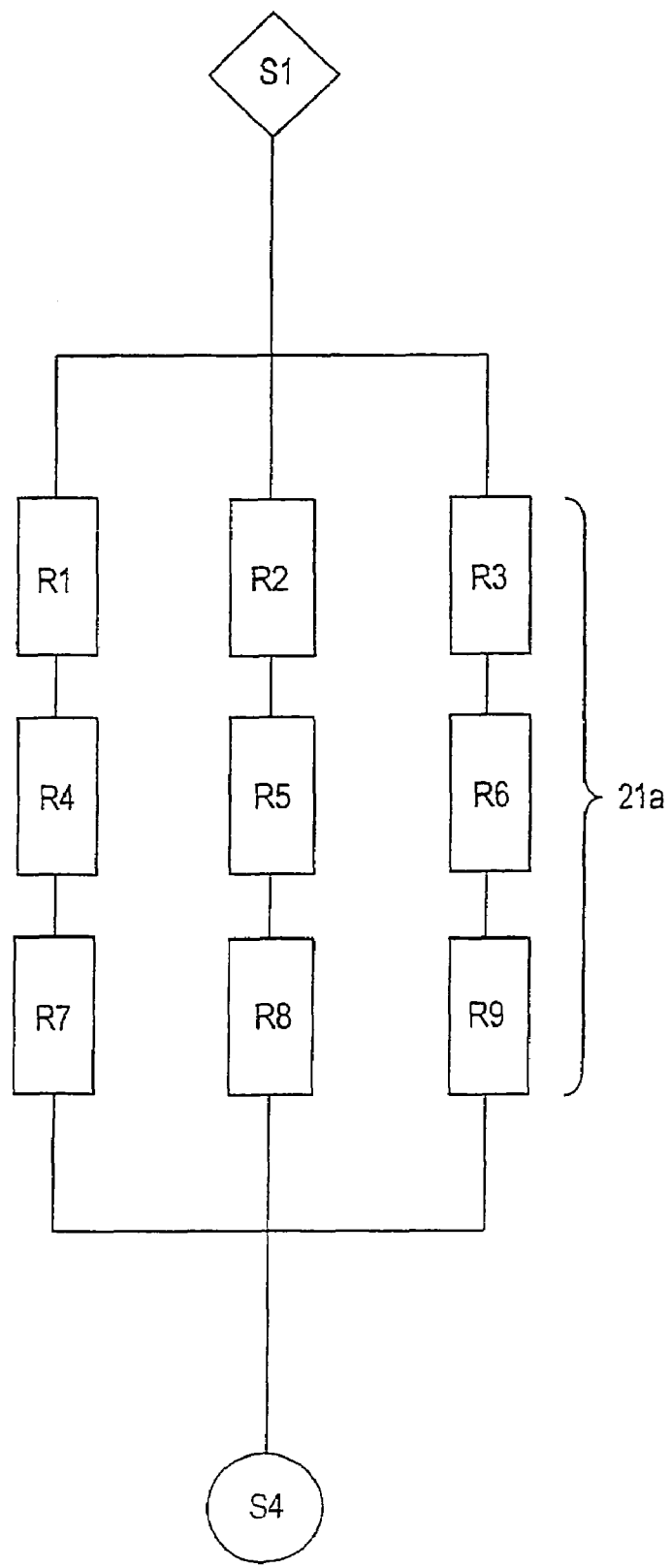
FIG. 4 is a schematic circuit diagram of an alternative part of the circuit diagram of FIG. 3 in accordance with the second embodiment of the invention.

In a refinement to the second embodiment of the invention two or more resistors can be used to reduce the power dissipated in each resistor, therefore allowing the use of smaller value resistors to provide the required high Ohmic value/low Wattage. An example of this is shown in FIG. 4 where a bank of resistors 21a (R1, R2, R3, R4, R5, R6, R7, R8 and R9) are shown replacing the single high value resistor 21 of FIG. 3. In this example, each of the resistors would only receive one third of the current and voltage (i.e. one ninth the power) of a typical self-test discharge and hence would only receive 1 kW of power if the whole network equalled a resistance of 50 Ohms, and only 1.1 W if the network resistance totalled 500K Ohms.

As will be appreciated, in order for the defibrillator to be capable of discharging energy over a relatively long period of time, it cannot discharge internally during treatment of a patient but must instead retain its charge in case it is required to e.g. defibrillate. However, following treatment of a patient or during a self-test there is no necessity to dump the charge quickly, and indeed where there is a bank of e.g. 4 capacitors, individual ones of such bank may be discharged individually whilst others in the same bank may be kept fully charged.

The foregoing leads to the concepts of the third embodiment of the invention which may also be illustrated by reference to FIG. 3 where it will be seen that each of the capacitors (C1, C2, C3 and C4) may be charged independently from the battery source via instructions from the processor 9 and the FET switches (F1, F2, F3 and F4) on the switch bank 20. In this embodiment the energy stored in each capacitor (C1, C2, C3, C4) is monitored by the processor 9 and each is charged from the battery 1 until a predetermined energy level is reached. At this point the processor 9 isolates the subject capacitor by deactivating the respective FET switch, and charges the next capacitor in the sequence.

In order to conserve energy the processor 9 may permit one capacitor to be fully charged prior to a self-test while the others in the bank are only partially charged such that during the self-test all capacitors in the capacitor bank 5 are discharged into an internal load such as the high value resistor 21, or alternatively, where the defibrillator is powered by a rechargeable battery, to the recycle circuit 8 of FIG. 1, such that various parameters of the discharge pulse can be monitored and measured during the test. For the next self-test the next capacitor in the bank can be fully charged and the others only partially charged, and so on, until all of the capacitors in the bank 4 have been tested at full charge, whereafter the process repeats.

Capacitor rotation during successive self-tests therefore allows for extended use of the battery whilst still facilitating the testing of each of the capacitors up to its respective maximum value over a required period of time. In addition, reliability of the self-test is ensured because all of the capacitors in the capacitor bank 4 are tested in each self-test. By utilising the concept of capacitor rotation it has been found that only approximately 60% of the energy that would ordinarily be required for a full self-test on all of the capacitors in the capacitor bank 4 is needed, whereas such a self-test would ordinarily be undertaken simultaneously on all capacitors in the bank.

In a fourth embodiment of the invention, which may again be illustrated by reference to FIG. 3, the switch bank 20 can be used to charge only one of the capacitors in the capacitor bank 4 at a time via instructions from the processor 9. During a self-test, the charged capacitor can then be discharged into the next successive capacitor, which is then discharged into the next, and so on, until all of the capacitors have been charged and discharged from, essentially, a single power input. By utilising capacitor rotation in this way, each capacitor can nevertheless still be checked for full discharge capability over a period of time and, but for capacitor leakage losses, it will be appreciated that only 25% of the initial full self-test energy is required, thereby prolonging the battery and/or permitting a smaller battery to be used than would otherwise be the case.

Figure 5:
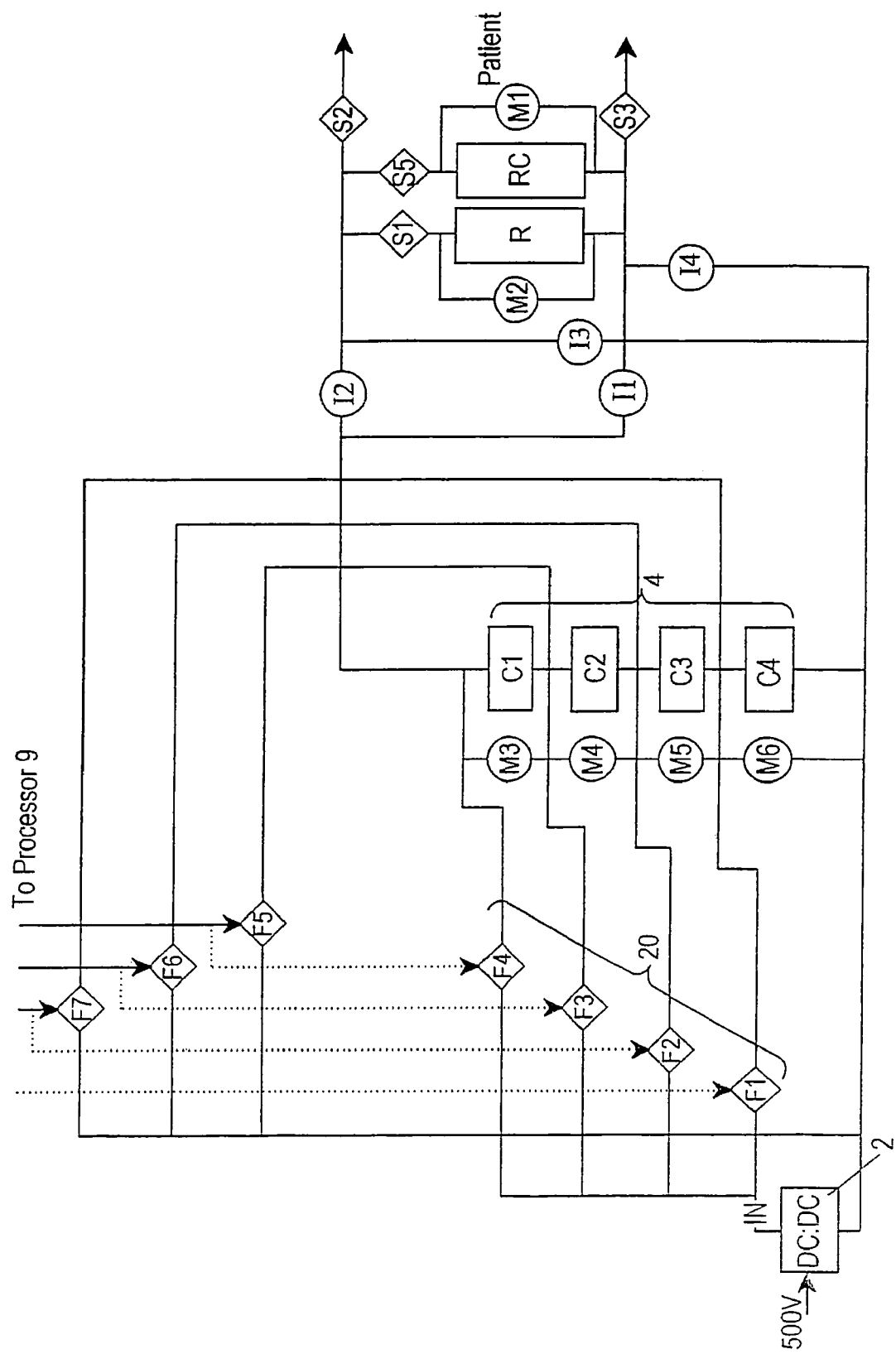
FIG. 5 is a schematic circuit diagram showing in combination the various embodiments of the invention.

Turning now to FIG. 5, this shows how the various embodiments of the invention may be combined within or as part of a circuit to allow for e.g. optional switching between energy recycling during a self-test as described with reference to FIGS. 1 and 2, or energy discharge/dumping as described with reference to FIGS. 3 and 4. In this circuit, where like parts are again numbered accordingly, the recycle circuit 8 is shown interposed in the circuit adjacent to switches S2 and S3, being activated and deactivated by switch S5. When activated, a measuring circuit M1 can be used to measure characteristics of the electrical energy discharged from the bank of capacitors 4 prior to it being recycled to the rechargeable battery supply (not shown). Similarly, a measuring circuit M2 can be used to measure parameters of the electrical energy discharged from the capacitor bank 4 during a self-test through the high value discharge resistor 21 when the switch S1 is open and the switch S5 is closed.

In order to measure the parameters of electrical energy discharged from each of the capacitors C1, C2, C3 and C4, respective measuring circuits M3, M4, M5 and M6 are interposed therebetween, although it will be appreciated that other circuit configurations may be employed including, for example, the use of a single measuring circuit across the whole bank of capacitors 4.

As will be apparent, a defibrillator incorporating the circuit of FIG. 5 can, if using rechargeable batteries, selectively benefit from the use of recycled electrical energy through the recycling circuit 8 during a self-test, thereby prolonging the original charge within the battery and making it possible e.g. to utilise smaller or fewer batteries than would otherwise be the case. However, irrespective of how the defibrillator is powered, Whether by primary cell, rechargeable cell or mains electricity, the electrical energy can also be discharged during a self-test via the high value discharge resistor 21 over a relatively long period of time, therefore obviating the need for a heat sink, with its attendant bulk and weight.

In all four embodiments of the invention, which may or may not be used independently or in combination where feasible, whether partially or wholly, it will be understood that the objectives of the invention may be realised by the provision of a defibrillator which is relatively small and lightweight as compared to conventional portable defibrillators, and may also be relatively inexpensive to produce and maintain.

The invention claimed is:

1. A portable defibrillator comprising:
   a processor and associated self-test circuit (1, 2, 3, 4, 5, 8 & 9) and comprising at least one capacitor (4), said self-test circuit being adapted to measure and monitor electrical energy discharged from said at least one capacitor (4); in which during the self-test electrical energy is discharged from said at least one capacitor (4) to a charge receiving circuit (5, 8 & 2) which recycles the energy back to a rechargeable battery supply (1) to thereby prolong the original charge within the battery.

2. A portable defibrillator according to claim 1, further comprising:
   the charge receiving and recycling circuit of claim 1 and a high Ohmic value discharge resistance such that the discharge occurs over a relatively long period of time, wherein provision is made in the circuitry of the defibrillator permitting optional switching (5, I1–I4, S1–S3, 21) of the discharged electrical energy during a self-test to either recycle it directly back to a rechargeable battery supply (1) or across the high value discharge resistance (21, 21*a*).

3. A portable defibrillator according to claim 1 further characterised in that the self-test is carried out on a bank of capacitors (4) in rotation such that for one self-test one capacitor is fully charged until a predetermined energy level is reached whilst the remaining capacitors in the bank are not, or may be only partially charged, and then following discharge during a self-test, the next capacitor in the bank is fully charged for discharge during the next self-test, the cycle repeating in sequence.

4. portable defibrillator according to claim 1, further characterised in that a single capacitor from a bank of capacitors (4) is fully charged as part of a self-test applied to a bank of capacitors (4) in rotation such that for one self-test one capacitor is fully charged until a predetermined energy level is reached whilst the remaining capacitors in the bank are not, or may be only partially charged, and then following discharge during a self-test, the next capacitor in the bank is fully charged for discharge during the next self-test, the cycle repeating in sequence;

but wherein during the self-test the single capacitor is discharged into the next capacitor, and so on, until all of the capacitors in the capacitor bank have been charged and discharged from substantially a single power input.

5. A portable defibrillator according to claim 1 further characterised in that measurement of the characteristics of a discharged pulse during a self-test occurs by the use of a measuring circuit (M3, M4, M5, M6) within the capacitor circuit.

6. A portable defibrillator according to claim 1 further characterised in that measurement of the characteristics of a discharged pulse during a self-test occurs by the use of a measuring circuit within the receiving circuit (M1, M2).

7. A portable defibrillator comprising:

a processor and associated self-test circuit (1, 2, 3, 4, 5, 9, 21 & 21*a*) and comprising at least one capacitor (4), said self-test circuit being adapted to measure and monitor electrical energy discharged from said at least one capacitor (4); in which during the self-test electrical energy is discharged from said at least one capacitor (4) to a charge receiving circuit (I1–I4, S1–S3, 21, 21*a*) containing a relatively high Ohmic value discharge resistance (21, 21*a*) such that the discharge occurs over a relatively long period of time and such that the discharge is unsuitable for life-saving-defibrillating use.

8. A portable defibrillator according to claim 7 further characterised in that the high value resistance comprises a single high value resistor (21).

9. A portable defibrillator according to claim 7 further characterised in that the high value resistance comprises a network (21*a*) of at least two smaller value resistors.

* * * * *